(12) United States Patent
McKay

(10) Patent No.: US 9,622,872 B2
(45) Date of Patent: Apr. 18, 2017

(54) INTERVERTEBRAL SPINAL IMPLANT AND METHOD

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 17 days.

(21) Appl. No.: 14/494,369

(22) Filed: Sep. 23, 2014

(65) Prior Publication Data

US 2016/0081811 A1    Mar. 24, 2016

(51) Int. Cl.
*A61F 2/44* (2006.01)
*A61F 2/46* (2006.01)
*A61F 2/30* (2006.01)
*A61B 17/70* (2006.01)

(52) U.S. Cl.
CPC ............ *A61F 2/44* (2013.01); *A61B 17/7071* (2013.01); *A61F 2/30749* (2013.01); *A61F 2/46* (2013.01); *A61F 2002/30069* (2013.01); *A61F 2002/30125* (2013.01); *A61F 2002/30224* (2013.01); *A61F 2002/30242* (2013.01); *A61F 2002/30565* (2013.01); *A61F 2002/30579* (2013.01)

(58) Field of Classification Search
CPC ............ A61F 2/44; A61F 2/30749; A61F 2/48
USPC .......................................... 623/17.13, 17.11
See application file for complete search history.

(56) References Cited

U.S. PATENT DOCUMENTS

| 5,653,763 | A | * | 8/1997 | Errico | A61F 2/446 411/55 |
| 5,980,522 | A | * | 11/1999 | Koros | A61F 2/4455 606/60 |
| 6,179,873 | B1 | * | 1/2001 | Zientek | A61F 2/4455 623/17.11 |
| 6,648,917 | B2 | * | 11/2003 | Gerbec | A61F 2/4455 623/17.11 |
| 6,709,458 | B2 | * | 3/2004 | Michelson | A61F 2/4455 623/17.11 |
| 6,773,460 | B2 | * | 8/2004 | Jackson | A61F 2/4455 623/17.11 |
| 6,962,606 | B2 | * | 11/2005 | Michelson | A61F 2/4455 623/17.11 |
| 7,214,243 | B2 | * | 5/2007 | Taylor | A61F 2/4425 623/17.11 |
| 7,344,564 | B2 | * | 3/2008 | Sweeney | A61F 2/446 623/17.11 |
| 7,674,296 | B2 | * | 3/2010 | Rhoda | A61F 2/44 623/17.11 |
| 7,678,116 | B2 | * | 3/2010 | Truckai | A61B 17/7095 606/92 |
| 7,708,779 | B2 | * | 5/2010 | Edie | A61F 2/44 623/17.11 |

(Continued)

*Primary Examiner* — Ellen C Hammond
*Assistant Examiner* — Stuart S Bray

(57) ABSTRACT

A spinal implant is provided. The spinal implant comprises a body configured for implantation between two adjacent vertebrae, and comprises a retaining member movable between a first position where the retaining member is in an unexpanded configuration and a second position where the retaining member is in an expanded configuration. The retaining member comprises a tissue contacting surface configured to engage a lamina of at least one of the adjacent vertebrae.

17 Claims, 7 Drawing Sheets

(56) References Cited

U.S. PATENT DOCUMENTS

| | | | |
|---|---|---|---|
| 7,722,674 B1* | 5/2010 | Grotz | A61F 2/446 623/17.11 |
| 7,731,751 B2* | 6/2010 | Butler | A61F 2/446 606/279 |
| 7,846,206 B2* | 12/2010 | Oglaza | A61F 2/44 606/246 |
| 7,879,099 B2* | 2/2011 | Zipnick | A61B 17/3421 606/79 |
| 7,883,542 B2* | 2/2011 | Zipnick | A61B 17/320016 623/17.11 |
| 7,922,750 B2 | 4/2011 | Trautwein et al. | |
| 7,993,375 B2* | 8/2011 | Bae | A61B 17/7007 606/246 |
| 7,998,174 B2* | 8/2011 | Malandain | A61B 17/025 606/249 |
| 7,998,208 B2* | 8/2011 | Kohm | A61B 17/025 606/279 |
| 8,007,521 B2* | 8/2011 | Malandain | A61B 17/025 606/249 |
| 8,012,207 B2* | 9/2011 | Kim | A61B 17/7065 623/1.15 |
| 8,062,375 B2* | 11/2011 | Glerum | A61F 2/447 606/279 |
| 8,236,031 B2 | 8/2012 | Bucci | |
| 8,398,713 B2* | 3/2013 | Weiman | A61F 2/44 623/17.11 |
| 8,425,559 B2* | 4/2013 | Tebbe | A61B 17/7062 606/248 |
| 8,518,114 B2* | 8/2013 | Marik | A61F 2/4425 623/17.11 |
| 8,518,120 B2* | 8/2013 | Glerum | A61F 2/447 606/279 |
| 8,556,979 B2* | 10/2013 | Glerum | A61F 2/4455 606/279 |
| 8,628,578 B2* | 1/2014 | Miller | A61F 2/447 623/17.11 |
| 8,685,095 B2* | 4/2014 | Miller | A61F 2/447 623/17.11 |
| 8,795,367 B2* | 8/2014 | Zipnick | A61B 17/320016 623/17.11 |
| 8,852,279 B2* | 10/2014 | Weiman | A61F 2/442 623/17.11 |
| 8,864,833 B2* | 10/2014 | Glerum | A61F 2/442 623/17.11 |
| 8,940,052 B2* | 1/2015 | Lechmann | A61F 2/442 606/246 |
| 9,039,771 B2* | 5/2015 | Glerum | A61F 2/447 623/17.11 |
| 2008/0228225 A1 | 9/2008 | Trautwein et al. | |
| 2009/0254122 A1 | 10/2009 | Khalife | |
| 2009/0281628 A1* | 11/2009 | Oglaza | A61B 17/7065 623/17.15 |
| 2011/0218572 A1 | 9/2011 | Lechmann et al. | |
| 2012/0215262 A1 | 8/2012 | Culbert et al. | |
| 2013/0184753 A1* | 7/2013 | Keiper | A61B 17/7047 606/248 |

* cited by examiner

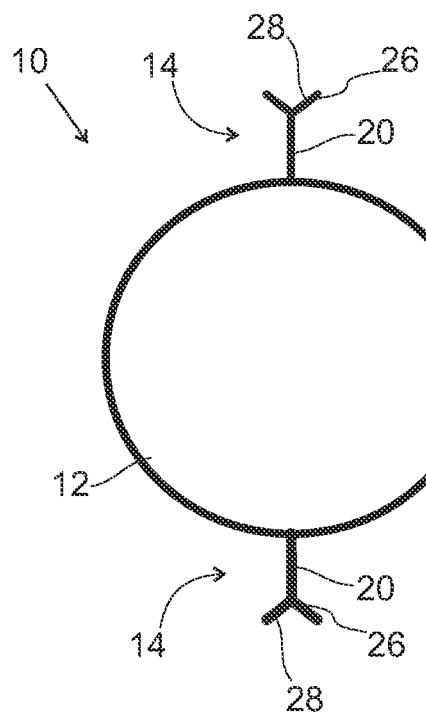
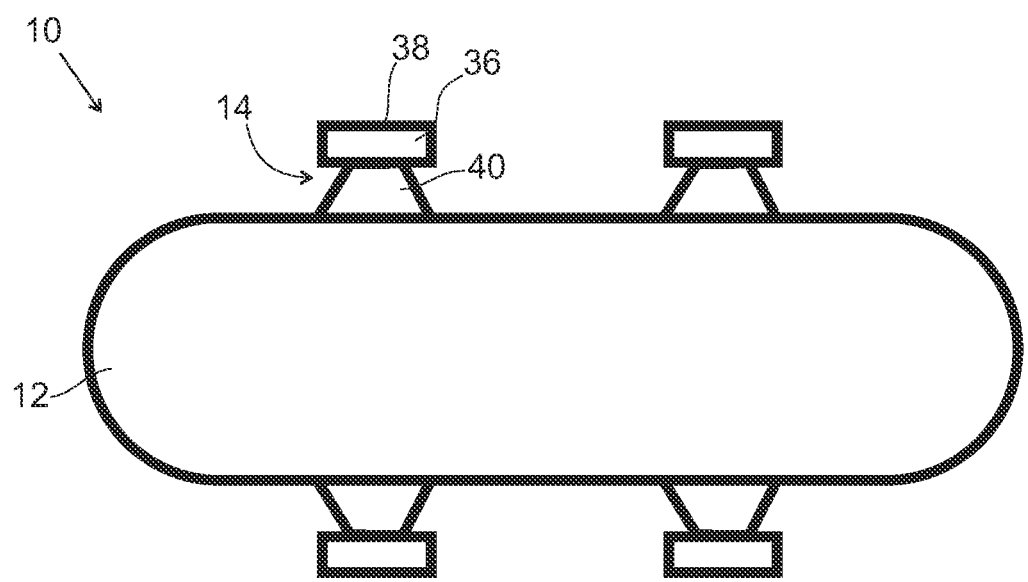

INTERVERTEBRAL SPINAL IMPLANT AND METHOD

BACKGROUND

The rapid and effective repair of bone defects caused by injury, disease, wounds, or surgery is a goal of orthopedic surgery. Toward this end, a number of bone implants have been used or proposed for use in the repair of bone defects including spinal stenosis. The biological, physical, and mechanical properties of the bone implants are among the major factors influencing their suitability and performance in various orthopedic applications.

Spinal stenosis is the narrowing of the spinal canal, which can lead to an impingement on the spinal cord and various nerves resulting in symptoms of moderate to extreme pain. Bone implants are used to alleviate symptoms associated with spinal stenosis. Bone implants are also used to repair bone that has been damaged by disease, trauma, or surgery. In some types of spinal fusion, for example, bone implants are used to replace the cushioning disc material between the vertebrae or to repair a degenerative facet joint.

During certain spinal corrective procedures, such as for example, alleviating spinal stenosis pain and/or a spinal fusion procedure, bone implants are positioned in an interspinous process space. The interspinous process bone implants attempt to lessen pain caused by spinal stenosis by redirecting pressure away from the foramina. Interspinous process bone implants can also be used to facilitate bone remodeling and new bone growth, and integration of the bone implant (e.g., allograft) into host bone. However, interspinous process implants carry several inherent drawbacks. Exemplary disadvantages of interspinous process bone implants include difficulty mechanically fixing the implant to the spinous processes; erosion of adjacent bone; and fracture of the spinous process due to the relatively thin and weak nature of the spinous processes.

The present disclosure offers several advantages over interspinous process implants to lessen pain caused by spinal stenosis and/or maintain an intervertebral space during fusion of adjacent vertebrae.

SUMMARY

The present disclosure includes a spinal implant configured for engagement with lamina bone, which is much closer to a neutral axis of the spine and has greater strength and rigidity than spinous processes. The spinal implant is expandable to a selected length to apply a distracting force on the lamina to reduce the amount of soft tissue that protrudes into the spinal canal and foramen, which can be a cause of the pain associated with spinal stenosis.

In some embodiments, the spinal implant of the present disclosure allows the load to be transferred away from the spinous process to the intervertebral foramen and/or lamina. This reduces the risk of fracture of the spinous process, and bone resorption problems resulting from spinous process fracture.

In some embodiments, there is a spinal implant comprising a body configured for implantation between two adjacent vertebrae, the body comprising a retaining member movable between a first position where the retaining member is in an unexpanded configuration and a second position where the retaining member is in an expanded configuration, the retaining member comprising a tissue contacting surface configured to engage lamina of at least one of the adjacent vertebrae.

In some embodiments, in accordance with the principles of the present disclosure, a spinal implant is provided. The spinal implant includes a retaining member movable between a first position where the retaining member is in an unexpanded configuration and a second position where the retaining member is in an expanded configuration. In one embodiment, the retaining member comprises a foot extendable from the body. In one embodiment, the retaining member comprises spikes configured to be embedded in the lamina of at least one of the adjacent vertebrae. In some embodiments, the retaining member comprises a concave surface configured to engage the lamina of at least one of the adjacent vertebrae.

In some embodiments, a spinal implant includes a body configured for implantation between two adjacent vertebrae. In some embodiments, the body comprises a cylindrical, ellipsoid, or spherical shape. In some embodiments, the body is configured for implantation between lamina of adjacent vertebrae.

In some embodiments, a spinal implant includes a retaining member movable between a first position where the retaining member is in an unexpanded configuration and a second position where the retaining member is in an expanded configuration. In some embodiments, the retaining member comprises an elastomeric material. In some embodiments, the retaining member is spring-loaded with the body. In some embodiments, the spinal implant includes jacking member pivotable to move the body between the first position and the second position. In some embodiments, the retaining member is pullable to move between the first position and second position. In some embodiments, the retaining member is lockable in the second position.

In some embodiments, a spinal implant includes a body configured for implantation between two adjacent vertebrae, the body comprising a retaining member. In some embodiments, the body comprises a plurality of retaining members. In some embodiments, at least one retaining member is positioned on a first side of the body and at least one retaining member is positioned on a second side of the body. In some embodiments, the body comprises 4 retaining members.

In some embodiments, in accordance with the principles of the present disclosure, a spinal implant is provided. The spinal implant comprises a body defining a longitudinal axis and is configured for implantation between lamina of adjacent vertebrae, the body comprising a plurality of retaining members movable between a first position where the retaining members are in an unexpanded configuration and a second position where the retaining members are in an expanded configuration, the retaining members oppositely positioned on the body such that at least one retaining member contacts a superior vertebra and at least one retaining member contacts an inferior vertebra, the body comprising a recess configured to receive an implantation.

In some embodiments, in accordance with the principles of the present disclosure, a method for treating a spinal disorder is provided. The method comprises positioning a spinal implant between adjacent vertebrae, the implant having a body comprising a retaining member movable between a first position where the retaining member is in an unexpanded configuration and a second position where the retaining member is in an expanded configuration.

In some embodiments, a method for treating a spinal disorder is provided. The method includes inserting an insertion tool into a cavity defined by the body and rotating the insertion tool to move the retaining member from the first position to the second position to contact a lamina of at least one of the adjacent vertebrae.

In some embodiments, a method for treating a spinal disorder is provided. The method includes inserting a surgical tool into the body and rotating an internal screw to move the retaining member from the first position to the second position to contact a lamina of at least one of the adjacent vertebrae.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

FIG. 1A shows an implant comprising a cylindrical shape having a diameter D1. FIG. 1B shows an implant comprising an ellipsoid shape having a diameter D2. FIG. 1C shows an implant comprising a spherical shape having a diameter D3.

FIG. 3 illustrates a front view of an embodiment of a spinal implant. The implant comprises at least two retaining members extending from opposite sides of the implant's body.

FIG. 4 illustrates a side view of an embodiment of a spinal implant. The implant comprises at least four retaining members extending from opposite sides of the implant's body.

Figure 1A:
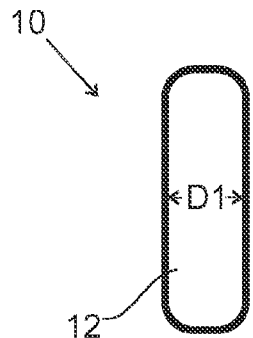
FIGS. 1A-1C illustrate top views of various configurations of a body of a spinal implant, as described herein. The body configurations shown comprise widening cross-section diameters.
Figure 1B:
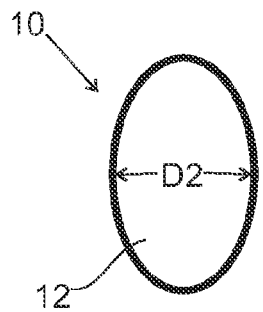
Figure 1C:
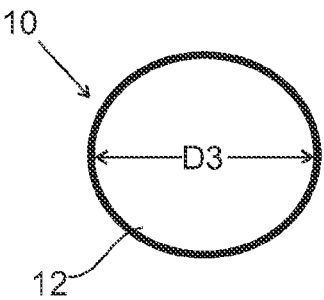

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. The following description is presented to enable any person skilled in the art to make and use the present disclosure.

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a spinal implant" includes one, two, three or more spinal implants.

For purposes of the description contained herein, with respect to components and movement of components described herein, "forward" or "distal" (and forms thereof) means forward, toward or in the direction of the forward or distal end of the probe portion of the device that is described herein, and "rearward" or "proximal" (and forms thereof) means rearward or away from the direction of the forward, or distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", or the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

"Biocompatible," as used herein, refers to materials that, upon administration in vivo, do not induce undesirable long-term effects.

"Bone," as used herein, refers to bone that is cortical, cancellous or cortico-cancellous of autogenous, allogenic, xenogenic, or transgenic origin.

"Demineralized," as used herein, refers to any material generated by removing mineral material from tissue, for example, bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the invention. In some embodiments, demineralized bone has less than 95% of its original mineral content. Demineralized is intended to encompass such expressions as "substantially demineralized," "partially demineralized," and "fully demineralized."

"Demineralized bone matrix," as used herein, refers to any material generated by removing mineral material from bone tissue. In preferred embodiments, the DBM compositions as used herein include preparations containing less than 5% calcium and preferably less than 1% calcium by weight. Partially demineralized bone (for example, preparations with greater than 5% calcium by weight but containing less than 100% of the original starting amount of calcium) are also considered within the scope of the invention.

"Mineralized" as used herein, refers to bone that has been subjected to a process that caused a decrease in their original organic content (e.g., de-fatting, de-greasing). Such a process can result in an increase in the relative inorganic mineral content of the bone. Mineralization may also refer to the mineralization of a matrix such as extracellular matrix or demineralized bone matrix. The mineralization process may take place either in vivo or in vitro.

"Osteoconductive," as used herein, refers to the ability of a non-osteoinductive therapeutic agent to serve as a suitable template or therapeutic agent along which bone may grow.

"Osteogenic," as used herein, refers to the ability of an agent, material, or implant to enhance or accelerate the growth of new bone tissue by one or more mechanisms such as osteogenesis, osteoconduction, and/or osteoinduction.

"Osteoimplant," as used herein, refers to any bone-derived implant prepared in accordance with the embodiments of this invention and therefore is intended to include expressions such as bone membrane, bone graft.

"Osteoinductive," as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference. In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. Percentage of osteoinductivity refers to an osteoinductivity score at a given time point expressed as a percentage of activity, of a specified reference score.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context. The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

Reference will now be made in detail to certain embodiments of the present disclosure, examples of which are illustrated in the accompanying drawings. While the present disclosure will be described in conjunction with the illustrated embodiments, it will be understood that they are not intended to limit the disclosure to those embodiments. On the contrary, the present disclosure is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

Spinal Implant

In one embodiment, a system for correcting a spinal abnormality, such as, for example, spinal stenosis is provided. The system includes an interlaminar distraction implant. In one embodiment, the implant includes an elastomeric or spring loaded member for lengthening the implant. In one embodiment, the implant includes an internal mechanical mechanism that lengthens the implant via a pre-tension mechanism. In one embodiment, the implant includes an expanding mechanism. In one embodiment, the implant is flexible. In one embodiment, the implant has a rigid structure.

In some embodiments, the spinal implant of the present disclosure allows load to be transferred away from the spinous process to the intervertebral foramen and/or lamina. This reduces the risk of fracture of the spinous process, and bone resorption problems resulting from spinous process fracture.

In one embodiment, the implant is inserted in a minimally invasively procedure. In some embodiments, the implant reduces spinal stenosis pain. The implant can be directly anchored into lamina bone and closer to a neutral axis of a spine. In some embodiments, the implant is distracted to a selected length while being anchored between lamina to reduce the amount of soft tissue that protrudes into a spinal canal and foramen, which is a cause of pain associated with spinal stenosis.

Referring to FIGS. 1-13, FIG. 1 illustrates a side view of embodiments of a spinal implant, such as, for example, a spacer 10. In this illustrated embodiment, spacer 10 comprises a body 12 configured for maintaining a space between vertebral tissue, such as, for example, adjacent lamina of a vertebrae V. In some embodiments, body 12 has a bullet-shaped configuration. In some embodiments, body 12 comprises an ellipsoid or spherical shape. In other embodiments, body 12 is variously configured, such as, for example, round, oval, oblong, square, triangular, rectangular, irregular, uniform, non-uniform, consistent, kidney-shaped and/or variable.

In various embodiments, body 12 comprises a cylindrical shape having diameter D1. Body 12 may include bullet shaped ends to facilitate insertion between adjacent lamina of vertebrae V while minimizing damage to surrounding tissue. Body 12 may include flat ends to create a slimmer profile to fit between an interlaminar space. In some embodiments, a leading end during insertion is bullet shaped and a trailing end during insertion is flat. In one embodiment, body 12 comprises an ellipsoid shape having diameter D2. Diameter D2 is wider than diameter D1 and configured to space an upper vertebra V1 and a lower vertebra V2 a greater distance than a spacer 10 having diameter D1. In one embodiment, body 12 comprises a spherical shape having diameter D3. Diameter D3 is wider than diameter D2 and configured to space an upper vertebra V1 and a lower vertebra V2 a greater distance than a spacer 10 having diameter D2.

Body 12 may be configured to facilitate gripping upper vertebra V1 and lower vertebra V2. In such an embodiment, body 12 may have alternate surface configurations, such as, for example, rough, arcuate, undulating, mesh, porous, semi-porous, dimpled and/or textured to facilitate gripping tissue to maintain spacer 10 in a desired position and orientation. In other embodiments, body 12 may be configured to have a smooth surface to facilitate ease of implantation into an interlaminar space.

Figure 2:
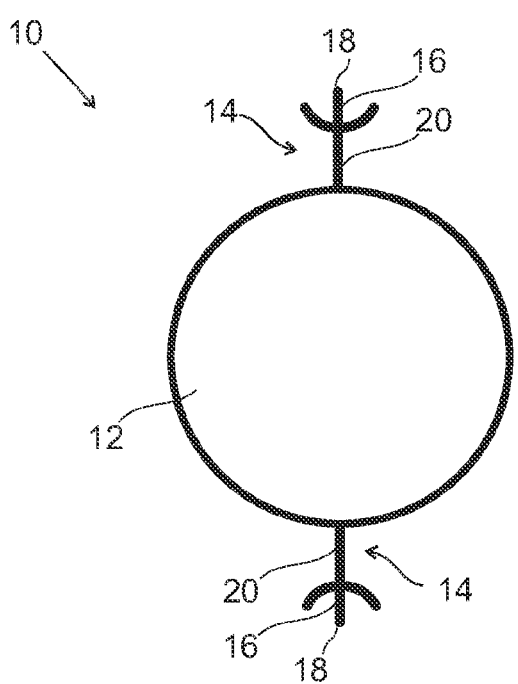
FIG. 2 illustrates a front view of an embodiment of a spinal implant. The implant comprises at least two retaining members extending from opposite sides of the implant's body.

As shown in FIGS. 2-5, spacer 10 includes at least one retaining member 14 configured to engage an inferior surface of an upper lamina L1 and/or a superior surface of a lower lamina L2. In some embodiments, as shown in FIG. 2, a spacer 10 includes retaining members 14 having spikes 16 for engagement with lamina L1 and/or L2. Spikes 16 are configured to be embedded in an upper lamina L1 or a lower lamina L2. Spikes 16 define engagement surface 18 for contacting lamina L1, L2, as disclosed herein. Engagement surface 18 may be configured to comprise a gripping surface to facilitate engagement with lamina L1, L2. Engagement surface 18 may comprise a polymer coating configured to release an active agent. Examples of suitable biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns. In some embodiments, the range of the coating on engagement surface 18 ranges from about 5 microns to about 250 microns or 5 microns to about 200 microns. Retaining member 14 protrudes from body 12 via support 20, such that support 20 extends a distance from body 12 to allow spikes 16 to engage lamina L1, L2.

In some embodiments, as shown in FIG. 3, a spacer 10 includes retaining members 14 having a receiving body 26 for engagement with lamina L1 and/or L2. Receiving body 26 defines a concave engagement surface 28 for contacting lamina L1, L2, as disclosed herein. Retaining member 14 protrudes from body 12 via support 20, such that support 20 extends a distance from body 12 to allow engagement surface 28 to engage lamina L1, L2. Engagement surface 28 may be configured to comprise a gripping surface to facilitate engagement with lamina L1, L2. Engagement surface 28 may comprise a polymer coating configured to release an active agent, as described above.

Figure 5:
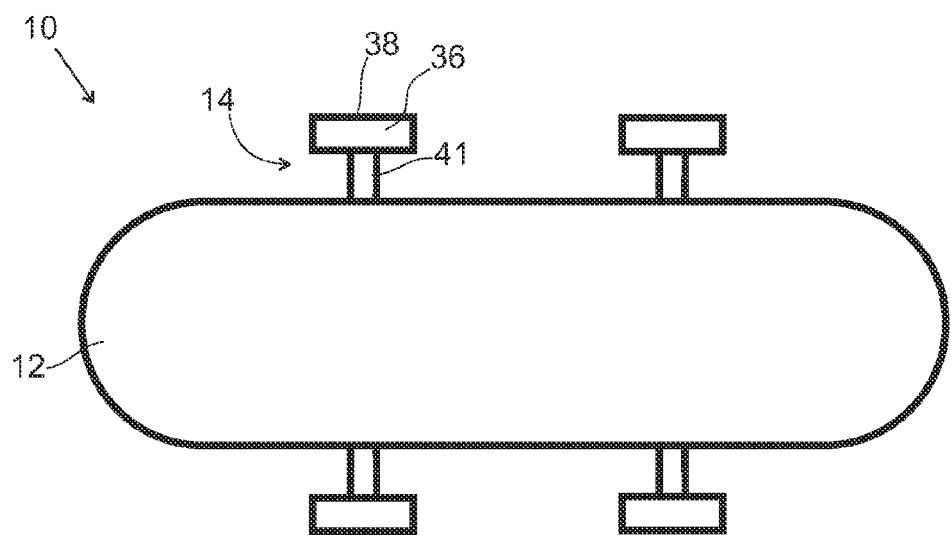
FIG. 5 illustrates a side view of an embodiment of a spinal implant. The implant comprises at least four retaining members extending from opposite sides of the implant's body.

In some embodiments, as shown in FIGS. 4-5, a spacer 10 includes retaining members 14 having a foot 36 for engagement with lamina L1 and/or L2. Foot 36 defines engagement surface 38 for contacting lamina L1, L2, as disclosed herein. As shown in FIG. 4, retaining member 14 protrudes from body 12 via support 40, such that support 40 extends a distance from body 12 to allow engagement surface 38 to engage lamina L1, L2. Support 40 comprises a wide base attached to body 12 to provide for a sturdy connection with lamina L1, L2. As shown in FIG. 5, retaining member 14 protrudes from body 12 via support 41, such that support 41 extends a distance from body 12 to allow engagement surface 38 to engage lamina L1, L2. Support 41 comprises a low profile support configured to engage lamina L1, L2. In some embodiments, support 41 is configured to slide into a notch cut into a lamina during a surgical procedure, as described herein. Engagement surface 38 may comprise a gripping surface to facilitate engagement with lamina L1, L2. Engagement surface 38 may comprise a polymer coating configured to release an active agent, as described above.

In various embodiments, body 12 comprises one retaining member 14 configured to engage an inferior surface of an upper lamina L1 and/or a superior surface of a lower lamina L2. In such an embodiment, the retaining member 14 may be configured in the center of an upper or lower surface of body 12. In various embodiments, body 12 comprises one retaining member 14 on an upper surface of body 12 and one retaining member 14 on a lower surface of body 12. In various embodiments, body 12 comprises two spaced apart retaining members 14 on an upper surface of body 12 and two spaced apart retaining members 14 on a lower surface of body 12. It is contemplated that body 12 may have more or less retaining members 14 spatially arranged to engage lamina L1, L2.

Retaining members 14 can comprise elastomeric material of synthetic or natural origin configured to have the ability to respond rapidly to mechanical stresses, particularly shears and loads, in the human body. In various embodiments, retaining members 14 are flexible and compressible to facilitate implantation and retention in an interlaminar space. In various embodiments, the elastomeric material comprises PEEK-BaSO4 polymeric rubbers, polyethylene terephthalate (PET), silicone, polyurethane, silicone-polyurethane copolymers, polymeric rubbers, polyolefin rubbers, semi-rigid and rigid materials, elastomers, rubbers, thermoplastic elastomers, thermoset elastomers, or other elastomeric composites. The elastomeric characteristics impart shock absorbent capabilities onto spacer 10.

Figure 6:
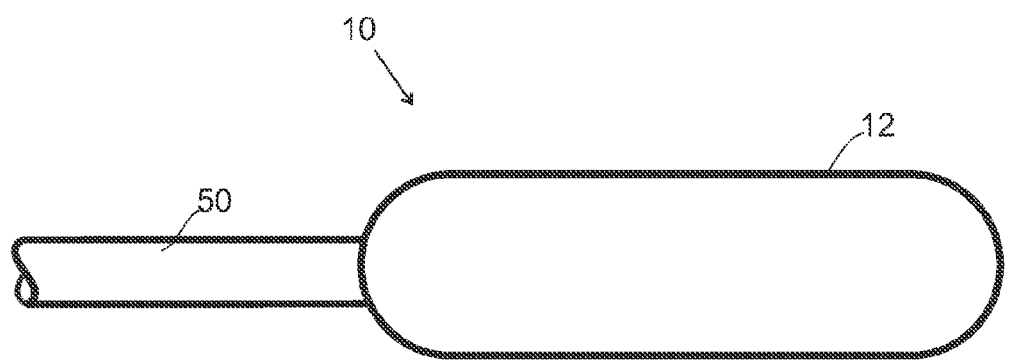
FIG. 6 illustrates a side view of an embodiment of a spinal implant. The implant is configured to receive an insertion tool to facilitate insertion into an interlaminar space.

In some embodiments, as shown in FIG. 6, an insertion tool 50 is engageable with body 12 to facilitate with insertion of spacer 10 into an interlaminar space and the expansion of retaining members 14. In various embodiments, insertion tool 50 includes, but is not limited to, a driver, wrench, spanner, screwdriver, or other turning tool, and the like that can engage body 12. Insertion tool 50 may be used manually (e.g., turnable by hand) or by an automatic device (e.g., using a drill, power driver, etc.). Insertion tool 50 may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. In various embodiments, insertion tool 50 is not biodegradable.

Figure 7:
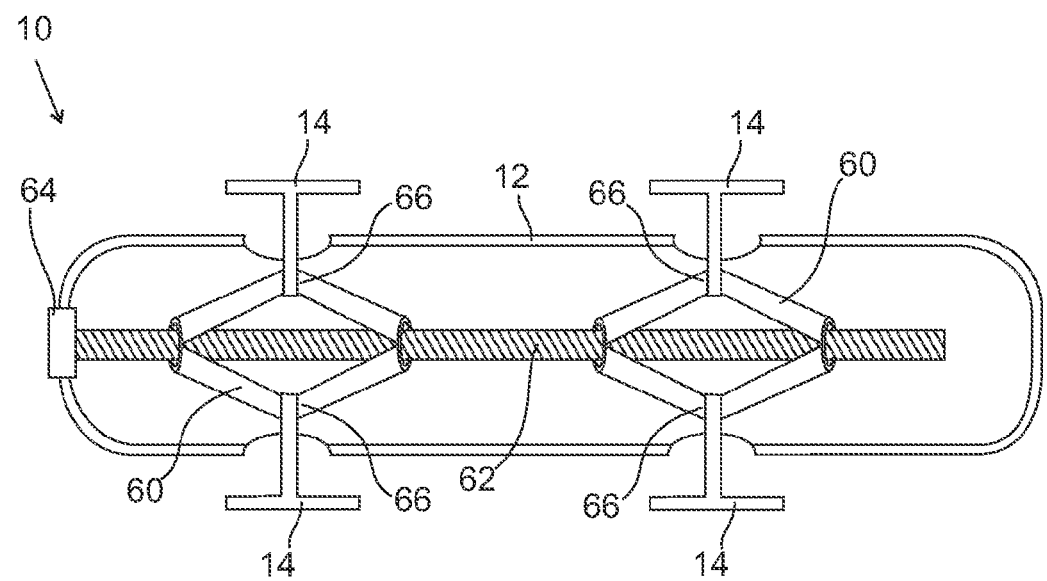
FIG. 7 illustrates a side cross-sectional view of a spinal implant having an internal screw rotatably attached to jacking members. The jacking members are coupled to the retaining members. The jacking members pivot as the screw is turned to move the retaining members between a first and second configuration.

As illustrated in FIG. 7, in some embodiments, body 12 may include jacking members 60 configured for engagement with insertion tool 50. Retaining members 14 are expandable relative to body 12 via jacking members 60 between an unexpanded position and an expanded position. Jacking members 60 are connected to a screw 62 disposed in coaxial alignment with bore 64. Screw 62 includes a head configured for mating engagement with a distal end of insertion tool 50 to rotate screw 62 within bore 64. Jacking members 60 includes a pair of hinges 66 connected with oppositely disposed retaining members 14. Screw 62 is threadedly engaged to a pivot point of hinges 66 such that the rotation of screw 62 causes hinges 66 to flex outwardly or inwardly to drive the relative axial movement of retaining members 14. In some embodiments, jacking member 60 is variously configured, such as, for example, as a bell crank, cam, connection rod, crank arm, jack, radius bar, winch, a series of gears or a yoke.

In some embodiments, insertion tool 50 is insertable into bore 64 such that upon rotation of insertion tool 50, screw 62 is rotatable in a first direction to move retaining members 14 from the unexpanded to expanded configuration. Screw 62 is rotatable in a second direction to move retaining members 14 from the expanded configuration to the unexpanded configuration.

Figure 8:
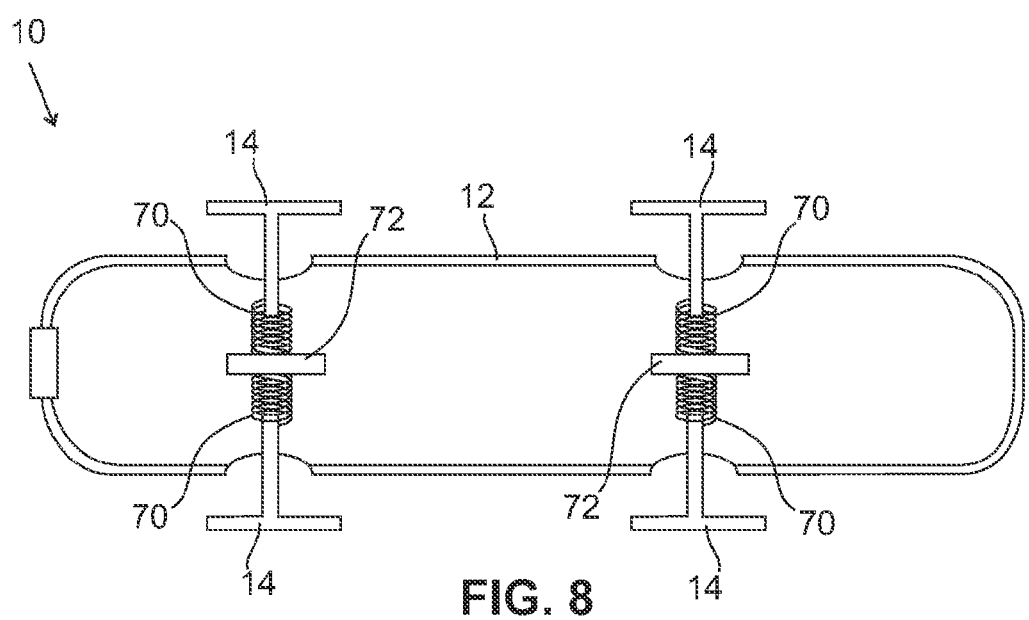
FIG. 8 illustrates a side cross sectional view of a spinal implant having biasing members attached to the retaining members. The biasing members are resiliently biased to maintain the retaining members in the expanded configuration.

As illustrated in FIG. 8, in some embodiments, body 12 may include biasing members 70 attachable to retaining members 14. In some embodiments, biasing members 70 comprise springs. In some embodiments, biasing members 70 are resiliently biased to maintain retaining members 14 in the expanded configuration. Retaining members 14 are movable to the unexpanded configuration upon being acted on by a downward force to compress biasing member 70. Biasing members 70 each comprise a first end that is attached to a wall 72 and a second end attached to a retaining member 14. Wall 72 provides leverage for biasing members 72 to facilitate maintaining the retaining members 14 in the expanded configuration. In some embodiments, as shown in FIG. 8, body 12 comprises two spaced apart walls 72 positioned between oppositely disposed retaining members 14.

Figure 9:
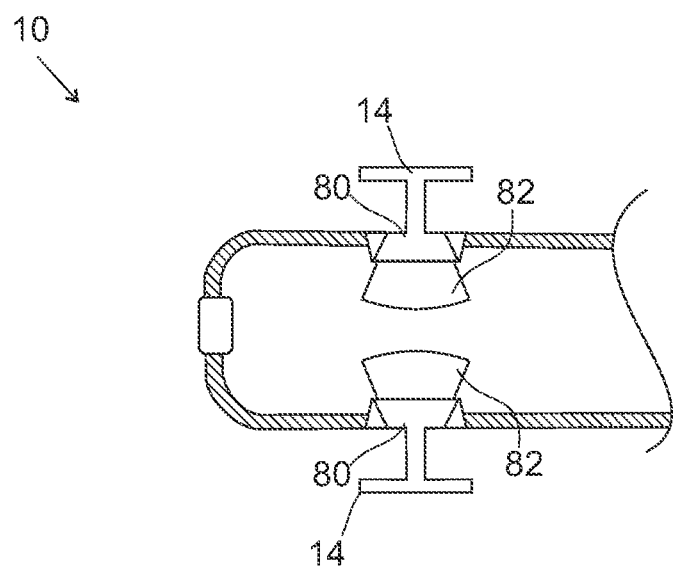
FIG. 9 illustrates a break away side cross sectional view of a spinal implant having retaining members comprising frustoconical bases that lock the retaining members in the expanded configuration.

In various embodiments, retaining members 14 are lockable in the expanded configuration. FIG. 9 illustrates retaining members 14 that are pullable between the expanded and unexpanded configurations such that when pulled to the expanded configuration, retaining members 14 are locked in the expanded configuration. Each retaining member 14 comprises a frustoconical base 80 configured for disposal in a corresponding frustoconical-shaped cavity 82. In some embodiments, each frustoconical base 80 comprises an elastomeric material such that frustoconical bases 80 are slightly deformable to facilitate being pulled out of cavities 82, but possess rigid qualities to prevent retaining members from being pushed back into cavities 82. Once pulled into the locked position, bases 80 are disposed into locking cavities 84. Locking cavities 84 are sized to rigidly receive bases 80 of retaining members 14 to prevent lateral or axial movement of retaining members 14.

Figure 10:
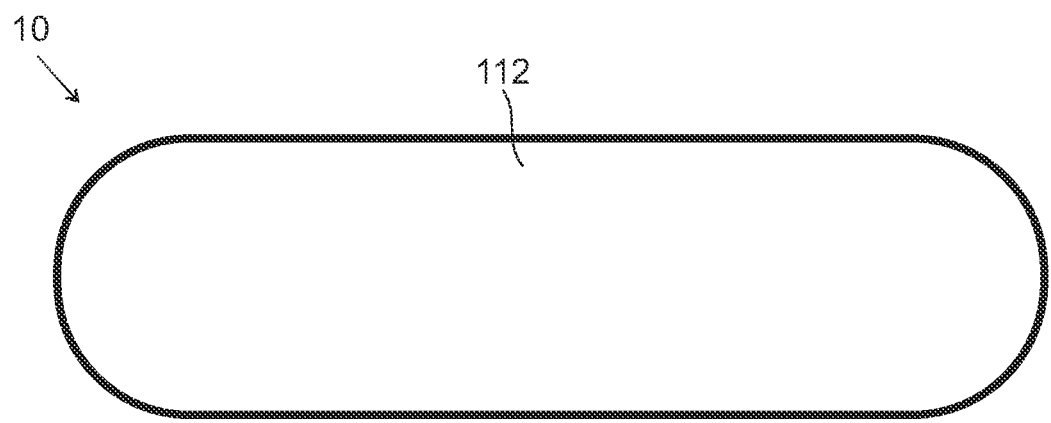
FIG. 10 illustrates a top view of an embodiment of a spinal implant. The implant comprises a curved shape to facilitate implantation into deep interlaminar spaces.
Figure 11:
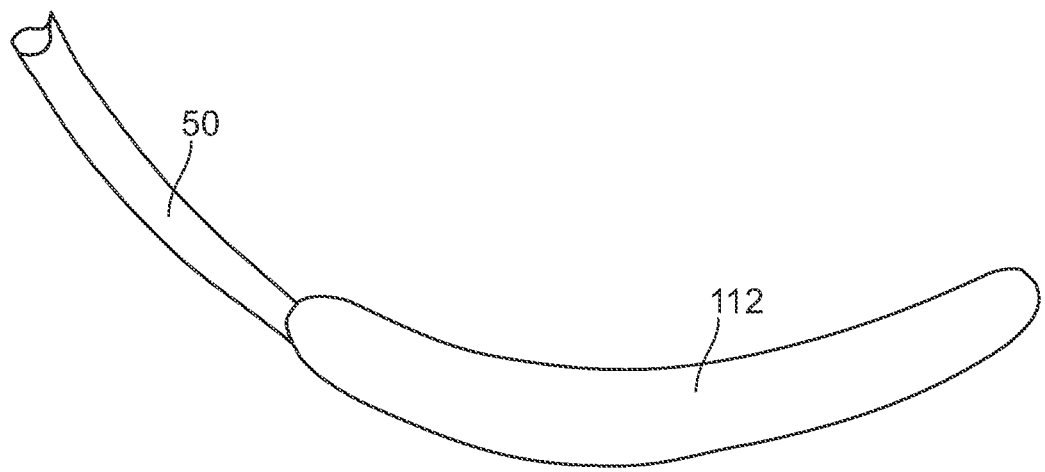
FIG. 11 illustrates a top view of an embodiment of a spinal implant. The implant comprises a curved shape to facilitate implantation into deep interlaminar spaces. The implant is configured to receive an insertion tool to facilitate insertion into an interlaminar space.

As shown in FIGS. 10 and 11, spacer 10 may comprise a curved body 112 similar to body 12. Body 112 may include bullet shaped ends to facilitate insertion between adjacent lamina of vertebrae V while minimizing damage to surrounding tissue. Body 112 may include flat ends to create a slimmer profile to fit between an interlaminar space. In some embodiments, a leading end during insertion is bullet shaped and a trailing end during insertion is flat. Body 112 comprises a curved configuration to facilitate lateral or posterolateral insertion of spacer 10 around a spinous process. In various embodiments, body 112 is configured for insertion into an interlaminar space in the lumbar, thoracic, or cervical vertebrae. In various embodiments, body 112 is configured for insertion at or above the L3 vertebra. In some embodiments, as shown in FIG. 8, an insertion tool 50 is engageable with body 112 to facilitate with insertion of spacer 10 into an interlaminar space and the expansion of retaining members 14.

The spinal implants provided allow for inter-laminar distraction to decompress nerves causing pain (e.g., disc herniation/bulging, hypertrophic ligaments and/or facets, stenosis, facet degeneration/slippage, etc.). The spinal implants provided, in some embodiments, are implanted in the midline of the posterior spinal column.

Materials

In various embodiments, body 12 comprises at least one of stainless steel alloys, commercially pure titanium, titanium alloys, Grade 5 titanium, cobalt-chrome alloys, stainless steel alloys, calcium phosphate, polyaryletherketone (PAEK), polyetheretherketone (PEEK), polyetherketoneketone (PEKK), polyetherketone (PEK), carbon-PEEK composites and PEEK-BaSO4.

In some embodiments, body 12 may be made from materials, such as for example, polyurethane, polyurea, polyether(amide), PEBA, thermoplastic elastomeric olefin, copolyester, and styrenic thermoplastic elastomer, metal alloys with high non-ferrous metal content and a low relative proportion of iron, carbon fiber, glass fiber, plastics, ceramics or combinations thereof.

In various embodiments, some or all of body 12 may comprise material that is bioresorbable. Examples of suitable biodegradable and/or bioresorbable material include, but is not limited to, poly (alpha-hydroxy acids), poly (lactide-co-glycolide) (PLGA), polylactide (PLA), polyglycolide (PG), polyethylene glycol (PEG), conjugates of poly (alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, or combinations thereof. In some embodiments, some or all of body 12 may comprise material that is shape memory material. Examples of suitable shape memory materials include, but are not limited to shape memory alloys such as nickel-titanium alloys (e.g., Nitinol), copper-aluminum-nickel, copper-zinc-aluminum, and iron- manganese-silicon alloys and shape memory polymers such as polyurethanes, polyurethanes with ionic or mesogenic components, block copolymers comprising polyethyleneterephthalate and polyethyleneoxide, block copolymers containing polystyrene and polybutadiene, polyesterurethanes with methylenebis and butanediol, epoxy resins.

In some embodiments, body 12 may comprise particles of bone-derived materials obtained from obtained from autograft, allograft, xenograft or transgenic cortical and/or corticocancellous bone sources. The bone-derived material may include one or more of non-demineralized bone particles, demineralized bone particles, lightly demineralized bone particles, and/or deorganified bone particles. Demineralized bone matrix preparations have been used for many years in orthopedic medicine to promote the formation of bone. Demineralized bone matrices promote bone formation in vivo by osteoconductive and osteoinductive processes. Osteoconduction occurs if the implanted material serves as a scaffold for the support of new bone growth. Osteoconduction is particularly significant when bone growth is desired across a large or "critical size" defect, across which bone healing would proceed only slowly or not at all. It is generally believed that the osteoconductive properties of demineralized bone matrix preparations are provided by the actual shape and coherence of the implant. Stabilizing agents, which tend to preserve the shape and/or coherence of the demineralized bone matrix substituent, can lead to better bone forming properties.

Any of a variety of bone matrix preparations may be utilized in the practice of the present invention. In certain preferred embodiments demineralized bone matrix is used. Demineralized bone matrix prepared by any method may be employed including particulate or fiber-based preparations, mixtures of fiber and particulate preparations, fully or partially demineralized preparations, mixtures of fully and partially demineralized preparations, including surface demineralized preparations.

The mixture of demineralized and mineralized bone fibers may be subjected to a configuring step to form an implant. The configuring step can be employed using conventional equipment known to those skilled in the art to produce a wide variety of geometries, for example, concave or convex surfaces, stepped surfaces, cylindrical dowels, wedges, blocks, screws, and the like. Also useful are demineralized bone and other matrix preparations comprising additives or carriers such as binders, fillers, plasticizers, wetting agents, surface active agents, biostatic agents, biocidal agents, and the like. Some exemplary additives and carriers include polyhydroxy compounds, polysaccharides, glycosaminoglycan proteins, nucleic acids, polymers, polaxomers, resins, clays, calcium salts, and/or derivatives thereof.

The DBM fibers may be present with cancellous bone chips. In some embodiments, the bone chips have a size of from about 1 mm to about 10 mm in diameter across their largest dimension or from about 2 mm to about 4 mm or from about 4 mm to about 6 mm or from about 6 mm to about 8 mm or from about 8 mm to about 10 mm across the largest dimension. A combined product of DBM fibers and cancellous bone chips is available as Grafton DBM®.

In some embodiments, the DBM fibers have an average length in the range of from about 250 micrometers to about 2 millimeters or from about 250 micrometers to about 750 micrometers or from about 750 micrometers to about 1.25 millimeters or from about 1.25 millimeters to about 2 millimeters.

As persons of ordinary skill in the art are aware, fibers have an aspect ratio, which is the average length to average thickness. In some embodiments, the aspect ratio is from about 4 to about 100 or from about 4 to about 25 or from about 25 to about 50 or from about 50 to about 75 or from about 75 to about 100.

In some embodiments, the average thickness of the fibers is from about 50 micrometers to about 250 micrometers or from about 50 micrometers to about 100 micrometers or from about 100 micrometers to about 150 micrometers or from about 150 micrometers to about 200 micrometers or from about 200 micrometers to about 250 micrometers.

Methods of Use

In assembly, operation and use, implantation of spacer 10 is employed with a surgical procedure for treatment of a spinal disorder affecting a section of a spine of a patient, as discussed herein. In use, to treat the affected section of vertebrae V, a medical practitioner obtains access to a surgical site including vertebrae V1, V2, comprising lamina L1, L2, respectively, in any appropriate manner, such as through incision and retraction of tissues. It is envisioned that spacer 10 may be used in any existing surgical method or technique including open surgery, mini-open surgery, minimally invasive surgery, and percutaneous surgical implantation, whereby vertebrae is accessed through a micro-incision. Once access to the surgical site is obtained, the particular surgical procedure is performed for treating the spinal disorder. Spacer 10 is then employed for implantation into an interlaminar space for the duration of a surgical procedure or for a duration of time extending beyond the period of the surgical procedure. Spacer 10 can be delivered or implanted as a pre-assembled device or can be assembled in situ. Spacer 10 may be completely or partially revised, removed or replaced during or after the surgical procedure.

Figure 12:
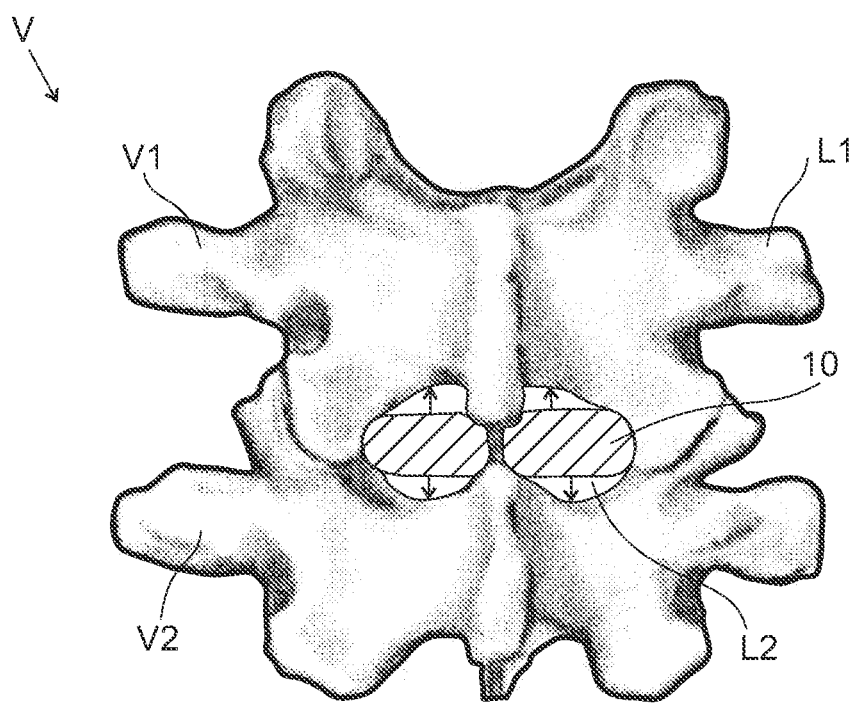
FIG. 12 illustrates a front plan view of an embodiment of a spinal implant that has been inserted into an interlaminar space.
Figure 13:
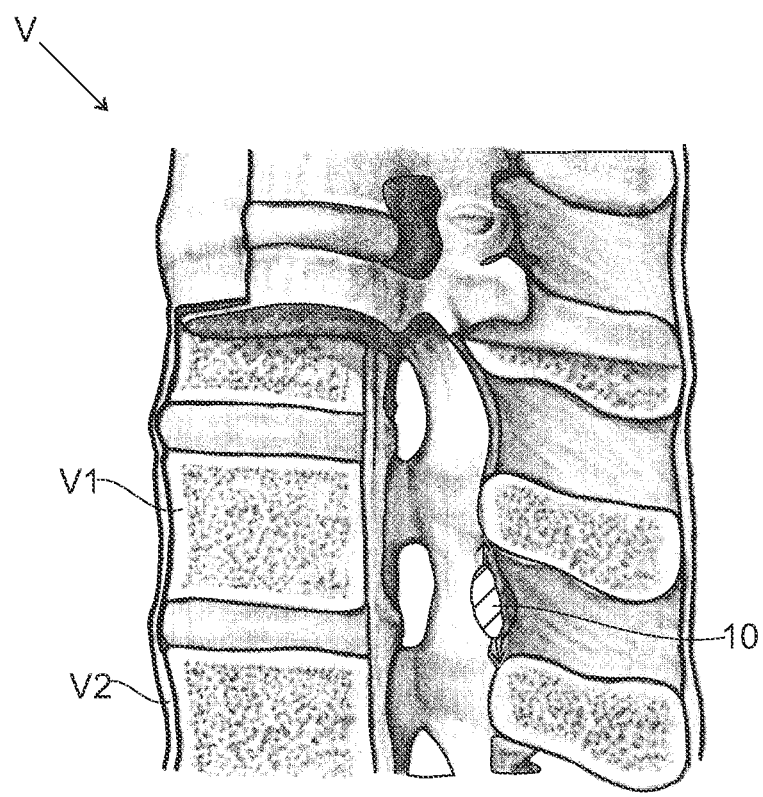
FIG. 13 illustrates a side plan view, in partial cross-section, of an embodiment of a spinal implant that has been inserted into an interlaminar space.

FIGS. 12 and 13 illustrate a method for treating a spine disorder, such as, for example, spinal stenosis pain. A medical practitioner obtains access to a surgical site including vertebrae V in any appropriate manner, such as through incision and retraction of tissues. In some embodiments, spacer 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

In some embodiments, an incision is made in a body of a patient and a cutting instrument (not shown) creates a surgical pathway along, in some embodiments, a substantially lateral or postero-lateral approach for implantation of components of spacer 10 within the patient body. Spacer 10 is oriented in the unexpanded position and is inserted substantially laterally through the surgical pathway. Spacer 10 is inserted along a surgical pathway that passes below the spinous process of upper vertebra V1 and into an interlaminar space between lamina L1, L2.

In some embodiments, spacer 10 includes jacking members 60 to move the retaining members between the unexpanded configuration and the expanded configuration. Spacer 10 is inserted into a desired position in an interlaminar space with the use of insertion tool 50. Insertion tool 50 is attached to body 12 at bore 64 in coaxial alignment with screw 62. Screw 62 is threadedly engaged to a pivot point of hinges 66 such that the rotation of screw 62 causes hinges 66 to flex outwardly or inwardly to drive the relative axial movement of retaining members 14. Insertion tool 50 is rotated while attached to body 12 to move retaining members 14 to the expanded configuration. Insertion tool 50 is rotated until a desired amount of detraction force is applied to lamina L1, L2 by spacer 10. Insertion tool 50 is detached from body 12 and the incision is closed by a medical practitioner.

In some embodiments, retaining members 14 are pullable between the expanded and unexpanded configurations such that when pulled to the expanded configuration, retaining members 14 are locked in the expanded configuration. Each retaining member 14 comprises a frustoconical base 80 configured for disposal in a corresponding frustoconical-shaped cavity 82. In such embodiments, the retaining members 14 are pulled from the unexpanded configuration to the expanded configuration in situ. The retaining members 14 can be pulled manually by a medical practitioner or with the use of a surgical tool (i.e., pliers, etc.). Retaining members 14 are locked in the expanded configuration so as to sustain compressive forces and distract lamina L1 from lamina L2 a desired distance.

In some embodiments, spacer 10 includes retaining members 14 having an engagement surface for contacting lamina L1, L2, as disclosed herein. The engagement surfaces each protrude from body 12 via a support, such that the supports extend a distance from body 12 to allow the engagement surface to engage lamina L1, L2. During or prior to the surgical procedure, a medical practitioner drills or cuts sagittal slots into lamina L1, L2 complementary to the profile of retaining members 14. During insertion, spacer 10 is positioned such that retaining members 14 align with the slots to define the insertion path of spacer 10 into an interlaminar space. Once aligned, retaining members 14 are slid into the slots to maintain a desired spacing between lamina L1, L2.

The dimensions of spacer 10 may be varied as required by a particular surgical procedure. For example, spacer 10 may have varying cross-sectional diameters to facilitate insertion into interlaminar spaces in different regions of the spine. In some embodiments, body 12 comprises a cylindrical shape having diameter D1. In some embodiments, body 12 comprises an ellipsoid shape having diameter D2. Diameter D2 is wider than diameter D1 and configured to space an upper vertebra V1 and a lower vertebra V2 a greater distance than a spacer 10 having diameter D1. In one embodiment, body 12 comprises a spherical or substantially spherical shape having diameter D3. Diameter D3 is wider than diameter D2 and configured to space an upper vertebra V1 and a lower vertebra V2 a greater distance than a spacer 10 having diameter D2. In some embodiments, an ellipsoid shaped body 12 may be used to space vertebrae L5 from S1 or L4 from L5. In some embodiments, spacer 10 having a curved body 112 is configured for insertion between two vertebrae at or above the L3 vertebra. Body 112 comprises a curved configuration to facilitate lateral or postero-lateral insertion of spacer 10 around a spinous process.

Radiographic markers can be included on spacer 10 to permit the user to accurately position spacer 10 into the desired site of the patient. These radiographic markers will also permit the user to track movement of spacer 10 at the site over time. In this embodiment, the user may accurately position spacer 10 in the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads. For example, the radiographic marker can be ring-shaped or dispersed as small pellets throughout spacer 10.

In various embodiments, spacer 10 may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of spacer 10 relative to the absence of the material or topography.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A spinal implant comprising a body configured for implantation between two adjacent vertebrae, the body comprising a first surface extending longitudinally and a retaining member having a second surface also extending longitudinally and being movable between a first position where the retaining member is in an unexpanded configuration and a second position where the retaining member is in an expanded configuration, the retaining member comprising a tissue contacting surface configured to engage a lamina of at least one of the adjacent vertebrae, wherein in an unexpanded configuration the second surface contacts and aligns with the first surface longitudinally, and in an expanded configuration, the retaining member protrudes from the first surface, and wherein the second surface has a smaller surface area than the surface area of the first surface.

2. A spinal implant according to claim 1, wherein the retaining member comprises a foot.

3. A spinal implant according to claim 1, wherein the retaining member comprises spikes configured to be embedded in the lamina of at least one adjacent vertebra.

4. A spinal implant according to claim 1, wherein the retaining member comprises a concave surface configured to engage a lamina of at least one adjacent vertebra.

5. A spinal implant according to claim 1, wherein the body comprises a cylindrical, ellipsoid, or spherical shape.

6. A spinal implant according to claim 1, wherein the retaining member comprises an elastomeric material.

7. A spinal implant according to claim 1, wherein the retaining member is spring-loaded with the body.

8. A spinal implant according to claim 1, further comprising a jacking member pivotable to move the second surface between the first position and the second position.

9. A spinal implant according to claim 1, wherein the retaining member is pullable to move between the first position and second position.

10. A spinal implant according to claim 1, wherein the retaining member is lockable in the second position.

11. A spinal implant according to claim 1, wherein the body comprises a plurality of retaining members and at least one retaining member is positioned on a first side of the body and at least one retaining member is positioned on a second side of the body.

12. A spinal implant according to claim 1, wherein the body comprises 4 retaining members.

13. A spinal implant according to claim 1, wherein the implant is configured for lateral or postero-lateral insertion into a surgical site.

14. A spinal implant comprising a body defining a longitudinal axis and configured for implantation between lamina of adjacent vertebrae, the body comprising a first surface extending longitudinally and a plurality of retaining members, each retaining member being T-shaped and having a second surface also extending longitudinally and being movable between a first position where the retaining members are in an unexpanded configuration and a second position where the retaining members are in an expanded configuration, the retaining members oppositely positioned on the body such that at least two retaining members contact a superior vertebra and at least two retaining members contact an inferior vertebra, the body comprising a recess configured to receive an implantation, wherein in an unexpanded configuration, the second surface contacts and aligns with the first surface longitudinally, and in an expanded configuration, the retaining members protrude from the first surface, and wherein the second surface has a surface area smaller than the surface area of the first surface.

15. A spinal implant according to claim 14, wherein the retaining members comprise feet, the feet defining a contacting surface disposable with the lamina of adjacent vertebrae.

16. A spinal implant according to claim 14, wherein the retaining members comprise spikes configured to be embedded in the lamina of adjacent vertebrae.

17. A spinal implant according to claim 14, wherein the retaining members comprise a concave surface configured to engage the lamina of adjacent vertebrae.

* * * * *